United States Patent [19]

Bastille

[11] Patent Number: 5,571,155
[45] Date of Patent: Nov. 5, 1996

[54] THERMO-PAD

[76] Inventor: Gilles Bastille, 48 Elizabeth Dr., Fort Payne, Ala. 35967

[21] Appl. No.: 264,110
[22] Filed: Jun. 22, 1994
[51] Int. Cl.⁶ ........................................................ A61F 7/00
[52] U.S. Cl. ............................................................... 607/114
[58] Field of Search ................................ 607/96, 108–112, 607/114

[56] References Cited

U.S. PATENT DOCUMENTS 2,783,807  3/1957  Duffield ................................... 607/112
4,592,358  6/1986  Westplate ............................. 607/114 X
5,300,104  4/1994  Gaudreault et al. ...................... 607/114

FOREIGN PATENT DOCUMENTS 2218908  11/1989  United Kingdom ..................... 607/114

Primary Examiner—Angela D. Sykes
Attorney, Agent, or Firm—Donald C. Casey

[57] ABSTRACT

A thermal pad is described for application to predetermined areas of the human body for therapeutic application of heat or cold. The pad of this invention includes a fabric cover which is porous and a heat medium filler for said cover. The filler of this invention consists of sterilized cereal grains, primarily oats and wheat.

12 Claims, 1 Drawing Sheet

THERMO-PAD

FIELD OF THE INVENTION

This invention relates to a therapeutic pad for external application to the human body for the application of heat or cold to an injured area. The pad of this invention may be heated in a microwave for use as a hot pad or cooled in a freezer for use as a cold pack and the heat transfer medium therein consists entirely of naturally occurring vegetable seeds.

DESCRIPTION OF THE PRIOR ART

As is well known, hot pads and cold packs have been in use in the treatment of a variety of afflictions for many years. Typically, hot pads have been electrically heated, and therefore involve very serious safety concerns. Care must be undertaken to avoid burning a patient who, for example, lies on the pad. Mobility of the user is restricted by the need to plug the pad into a source of electric energy. Such pads are also typically stiff because of the heating elements therein, and therefore are difficult to conform to specific areas of the human body to be treated.

Cold packs on the other hand typically have involved the use of ice which further requires a sealed container. As the ice melts, invariably the container will leak. Furthermore, as in the case of the electric heating pad, an ice pack does not easily conform to the contours of the human body to be treated.

In recent years, a gel-pack has been marketed which consists of a sealed, flexible container filled with a synthetic gel material which can be either heated in a microwave oven or frozen in the freezer. In U.S. Pat. No. 4,783,866 there is described a pillow with a removable therapeutic gel pack which contains a material marketed under the trademark "BLUE ICE" as the gel material. The patent also notes that prior art devices have used a mixture of starch, water and borax as a heat transfer medium. Similarly, in U.S. Pat. No. 4,865,012, the heat transfer medium described is a thickened saline solution wherein cellose and flour are added to provide the desired consistency. In U.S. Pat. No. 4,694,829 the heat transfer medium is salt dampened with polypropylene glycol and water so that it is pliable and somewhat mushy. U.S. Pat. No. 4,887,326 describes yet another type of synthetic gel containing cushion.

These prior art devices however have several disadvantages.

Desirably a hot or cold pack would be of particular use in treating arthritis and rheumatism, sprained ankles, sprained wrists and similar afflictions to the extremities. Also, hot packs in particular are useful in treating muscular pain associated with neck or back injuries, and internal conditions including menstrual cramps.

In each of these instances, the hot or cold pack is intended to have intimate contact with the skin surface. It is necessary then that it conforms to the surface configuration and that it has a smooth consistency for the user's comfort. Further, it is preferable to have a heat transfer medium that is not liquid so that if object is inadvertently punctured, leakage will not occur. Finally, it is particularly desirable that the object have substantial bulk density so that it will retain heat for a desired prior of time, or will remain cold likewise for a substantial period of time.

It has been discovered that the above disadvantages can be solved by utilizing a particulate material as the heat transfer medium enclosed within a porous skin and that a highly desirable particulate material is vegetable seeds such as corn, oats, wheat, rice and the like. Also, a U-shaped configuration has been found to be vastly superior in conforming to the contours of the human body.

The seeds contain sufficient moisture so that they can be heated in a microwave or cooled by freezing. The seeds further have sufficient bulk density so that they can be molded to conform to the configuration of a surface and are sufficiently small particles so that they provide a soft texture for the user. The device of this invention then is a pad of, for example, cotton fabric, which contains sterilized vegetable seeds in a preferred mixture. The device of this invention then may be heated in a microwave oven for example for no more than three minutes to provide a hot pad, or placed in a freezer for about six hours to provide a cold pack. The resulting pack can then be applied to the desired portion of the human body and retained by external wrapping. The external surface of course could be enclosed within a plastic sack or skin if desired and the overall device of this invention can have any desired external configuration from that of a pad to that of a "horse collar" for application to the neck area.

Accordingly, it is an object of this invention to provide a hot or cold pad which is manufactured from entirely naturally occurring materials and which may be easily conformed to the contours of the human body.

It is another object of this invention to provide a pad which can be heated in a microwave oven or cooled in a freezer and which will retain the hot or cold condition for a substantial period of time which is formulated from all natural materials using heat transfer medium of vegetable seeds.

It is a further object of this invention to provide a method for applying hot or cold compresses to the human body which comprises providing a fabric skin containing a mixture of particulate vegetable seeds in a desired volume which object is flexible for conforming to the contours of the human body, subjecting said object to microwave energy or freezing said object in a freezer and then directly applying said object to the involved area of the human body for a predetermined period of time.

These and other objects will become readily apparent with reference to the drawings and the following description wherein:

DETAILED DESCRIPTION OF THE INVENTION

Figure 1:
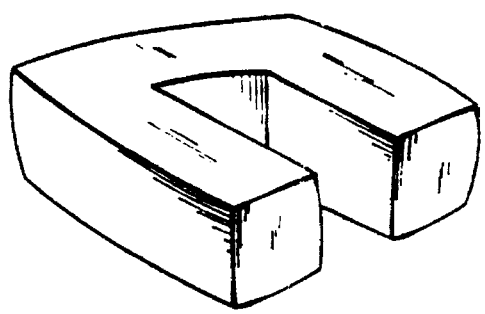
FIG. 1 is a perspective view of the preferred embodiment of this invention applied to the neck area of the human body.

With attention to the drawings, there are shown exemplary shapes of the thermal pad of this invention. Typically the U-shaped neck collar 10 of FIG. 1 would be about 22 inches long and about 2 inches thick. The longer pad, FIG. 2 could be 10 inches in diameter and 1 inch thick and the rectangular pad of FIG. 3 could be 8 inches by 10 inches by ¾ inch thick. It will be obvious to those skilled in the art that these dimensions are exemplary only and not intended to limit this invention. The device of this invention, in each instance, is a fabric cover stuffed with vegetable seeds in particular with selected sterilized cereal grains. Preferably the outer cover is made of cotton but other fabric could be used. Most importantly however the cereal grains used as stuffing are sterilized and completely fill the outer cover.

In the preferred embodiment, the grains used are sterilized Avena Sativa, Triticum, Zea Mays Rugosa; oats, wheat, and corn. In the preferred embodiment the product is primarily oats and can be up to about 95%. Preferably about 5% or slightly less wheat is added and a trace is corn. Corn is not essential, but may often be present in other cereal grains such as wheat. The total weight of the neck pad of FIG. 1 is about two pounds. It would be also within the scope of this invention to stuff the article of this invention with 100% oats, but the addition of wheat has been found to facilitate softness and ease of distribution when the article is configured about a portion of the human anatomy especially in the shape 10 of FIG. 1.

It is preferred if the article of this invention is to be heated, to use a microwave oven because of the speed at which the heat transfer medium, cereal grain, acquires the desired temperature. For example, with the pads of FIGS. 2–4, it is normally suggested that the pad be heated from 90 to a 120 seconds and that the pad then be checked for surface temperature. The pad should never be heated in a microwave oven more than three minutes, and, obviously, should always be handled carefully. Table I below illustrates the heat retention capability of the pads of this invention when heated in a microwave oven.

TABLE I

| RECTANGULAR PADS AND LONG PADS | | | | |
|---|---|---|---|---|
| Microwave Time | Average temp. at beginning | 15 min. | 30 min. | 45 min. |
| 2.5 minutes | 148° F. | 140° F. | 128° F. | 118° F. |
| 2.0 minutes | 130° F. | 128° F. | 120° F. | 118° F. |
| 1.5 minutes | 128° F. | 125° F. | 124° F. | 116° F. |

The thermal pad of this invention should not be left in a microwave beyond three minutes and if left for about 12 minutes will burst into flame.

If a microwave oven is not available a conventional oven preheated to 250° F. will suffice. When using a conventional oven, the pad of this invention should be placed in a glass or metallic container without touching any wall or electric element of the oven. The object should be heated then for 20 minutes and if not warm enough reheated at 250° F. for additional 15 minute increments. Table II below illustrates the heat retention capability for the article of this invention when heated in a convention oven.

TABLE II

| NECK MOLDED PAD | | | | |
|---|---|---|---|---|
| Microwave Time | Average temp. at beginning | 15 min. | 30 min. | 45 min. |
| 3.0 minutes | 148° F. | 145° F. | 138° F. | 125° F. |
| 2.5 minutes | 135° F. | 132° F. | 126° F. | 118° F. |
| 2.0 minutes | 122° F. | 120° F. | 118° F. | 110° F. |

In both instances when the product is heated in a microwave or in a conventional oven, the product should then be applied to the localized area. If the pad seems to loose its heat it should be shaken and then reapplied.

The pad also can be used as a cold pack and in that instance should be stored in a freezer in a plastic bag for about six hours. After freezing, the pad should applied in the conventional manner to the area of the human anatomy to be treated.

It is important to note that a pad which has been cooled in the freezer should not be placed directly into an oven or a microwave until it has completely thawed to room temperature. This may take at least about six hours. When the pad of this invention is not in use, it should be stored in a cool dry place in order to preserve the cereal grains therein.

As will be obvious to those skilled in the art, after a period of time wherein the heat transfer media, i.e., cereal grain, has been repeatedly heated and/or frozen, the pad may loose its ability to retain heat with its original efficiency. Because the product is entirely natural however it can be discarded without pollution considerations and is completely nontoxic.

While the outer covering of the device of this invention is preferably a cotton fabric, if desired a washable additional outer covering may be used as desired.

Figure 2A:
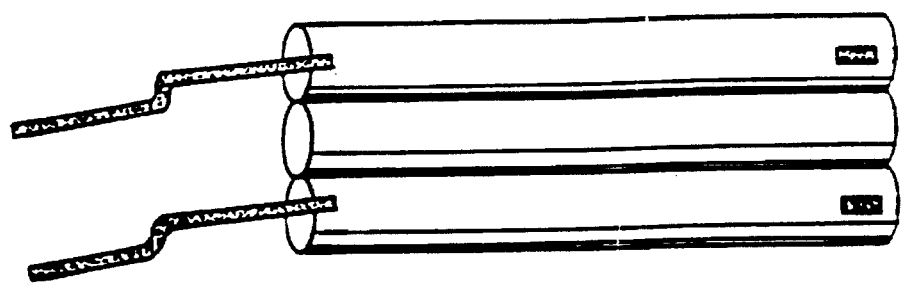
FIG. 2A is a perspective view of an alternate embodiment of this invention using Velcro closures.
Figure 2B:
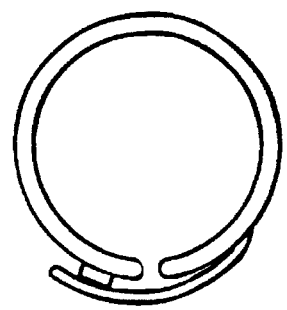
FIG. 2B is a view of FIG. 2A in a closed position to surround an injured limb.
Figure 3:
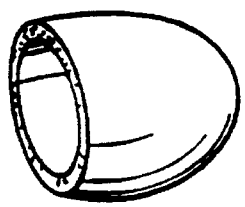
FIG. 3 is an alternative embodiment of a hand warmer.
Figure 4:
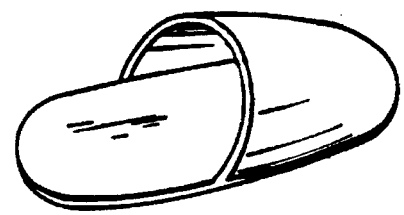
FIG. 4 is an alternative embodiment of a slipper.

Alternate designs for the device of this invention include, as shown in FIGS. 2–4, a relatively flat member 12 which uses Velcro fasteners 14 so that it may be used to encircle an injured limb such as a knee as shown in FIG. 2B. Preferably the design is not a flat pad but rather a plurality of interconnected cylinders 16, each of which contain cereal grains according to this invention.

In addition, the device of this invention may be configured as a hand warmer 18 or a slipper 20 or, in fact, any other, conventional design as will be obvious to those skilled in the art.

In summary, it has been discovered that a completely natural thermal pad can be provided which can function either as a hot or a cold pad in therapeutic application to selected portions of the human anatomy. The pad in this instance then is useful for treating a variety of maladies including rheumatism and arthritis, sprained ankles, pulled muscles, and the like. Furthermore, the device of this invention is provided in a U-shaped configuration to facilitate its application to the involved area of the human anatomy to be treated.

The device of this invention preferably is a cotton fabric covering in the desired shaped which is filled with sterilized vegetable seeds and most preferably cereal grains which are predominately oats. It has been found that particulate cereal grains are most desirable in that the product retains its bulk density while having a soft and resilient feeling and more than adequately functions as a heat transfer over extended periods of time to either supply heat to an area to be treated, or cold.

I claim:

1. A therapeutic pad for application of heat or cold to a predetermined potion of the human body comprising:
    a porous fabric cover having a predetermined three dimensional configuration and a heat transfer medium filing said cover, said medium consisting of cereal grains sterilized to destroy all living micro-organisms.
2. The pad of claim 1 wherein said medium is primarily oats.
3. The pad of claim 2 wherein the medium further comprises wheat.
4. The pad of claim 1 wherein said medium is about 95% oats, 4.5% wheat and 0.5% corn.
5. The pad of claim 1 wherein said cover is U-shaped.

6. The pad of claim 1 wherein said cover is rectangular and consists of a plurality of longitudinally interconnected cylinders.

7. The pad of claim 6 further comprising fastening means affixed to opposite ends of said cover.

8. The pad of claim 1 wherein said cover has a configuration adapted to receive a hand or foot therein.

9. Method of treating a predetermined area of the human body with heat or cold comprising the steps of;

providing a pad having a predetermined three-dimensional configuration filed with a heat transfer medium, said medium consisting of vegetable grain sterilized to destroy all living micro-organisms, heating or cooling said pad until said medium reaches a predetermined heat content; and topically applying said pad to said predetermined area of the human body.

10. The method of claim 9 wherein said medium is primarily oats.

11. The method of claim 10 wherein said medium further comprises wheat.

12. The method of claim 9 wherein said medium is about 95% oats, 4.5% wheat and 0.05% corn.

* * * * *